United States Patent
Chewter et al.

(10) Patent No.: US 10,294,181 B2
(45) Date of Patent: May 21, 2019

(54) PROCESS FOR THE PREPARATION OF GLYCOLS

(71) Applicant: SHELL OIL COMPANY, Houston, TX (US)

(72) Inventors: Leslie Andrew Chewter, Amsterdam (NL); Jean Paul Andre Marie Joseph Ghislain Lange, Amsterdam (NL); Duraisamy Muthusamy, Houston, TX (US); Timothy Michael Nisbet, Amsterdam (NL); Evert Van Der Heide, Amsterdam (NL); Pieter Huizenga, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days.

(21) Appl. No.: 16/060,221

(22) PCT Filed: Dec. 7, 2016

(86) PCT No.: PCT/EP2016/080116
§ 371 (c)(1),
(2) Date: Jun. 7, 2018

(87) PCT Pub. No.: WO2017/097847
PCT Pub. Date: Jun. 15, 2017

(65) Prior Publication Data
US 2018/0362424 A1 Dec. 20, 2018

(30) Foreign Application Priority Data
Dec. 9, 2015 (EP) ..................... 15198769

(51) Int. Cl.
| | | |
|---|---|---|
| *C07C 29/60* | (2006.01) | |
| *C07C 31/00* | (2006.01) | |
| *B01J 19/00* | (2006.01) | |
| *C07C 29/132* | (2006.01) | |
| *B01J 8/20* | (2006.01) | |
| *B01J 8/22* | (2006.01) | |
| *B01J 10/00* | (2006.01) | |
| *B01J 16/00* | (2006.01) | |
| *B01J 19/18* | (2006.01) | |
| *B01J 19/24* | (2006.01) | |
| *C07C 31/20* | (2006.01) | |

(52) U.S. Cl.
CPC ............... *C07C 29/132* (2013.01); *B01J 8/20* (2013.01); *B01J 8/22* (2013.01); *B01J 10/007* (2013.01); *B01J 16/005* (2013.01); *B01J 19/1881* (2013.01); *B01J 19/2465* (2013.01); *C07C 29/60* (2013.01); *C07C 31/202* (2013.01); *C07C 31/205* (2013.01); *B01J 2208/00283* (2013.01); *B01J 2219/0011* (2013.01); *C07C 2521/06* (2013.01); *C07C 2523/22* (2013.01); *C07C 2523/26* (2013.01); *C07C 2523/28* (2013.01); *C07C 2523/30* (2013.01); *Y02P 20/582* (2015.11)

(58) Field of Classification Search
CPC ....... C07C 29/60; C07C 29/141; B01J 19/1881
See application file for complete search history.

(56) References Cited

U.S. PATENT DOCUMENTS

| | | | |
|---|---|---|---|
| 2011/0313212 A1 | 12/2011 | Kalnes et al. | |
| 2015/0329449 A1 | 11/2015 | Schreck et al. | |

FOREIGN PATENT DOCUMENTS

| | | | |
|---|---|---|---|
| CN | 102643165 A | 8/2012 | |
| CN | 102675045 A | 9/2012 | |
| CN | 102731258 A | 10/2012 | |
| WO | 2012174087 A1 | 12/2012 | |
| WO | 2013015955 A2 | 1/2013 | |
| WO | 2015028398 A1 | 3/2015 | |

OTHER PUBLICATIONS

International Search Report and Written Opinion received for PCT Patent Application No. PCT/EP2016/080116, dated Feb. 8, 2017, 8 pages.
Ji et al., "Direct Catalytic Conversion of Cellulose into Ethylene Glycol Using Nickel-Promoted Tungsten Carbide Catalysts", Angewandte Chemie Int. Ed., Oct. 20, 2008, vol. 47, Issue No. 44, pp. 8510-8513.
Zhang et al., "Kinetic Study of Retro-Aldol Condensation of Glucose to Glycolaldehyde with Ammonium Metatungstate as the Catalyst", AIchE Journal, Nov. 2014, vol. 60, Issue No. 11, pp. 3804-3813.
Zhang et al., "Kinetic Study of the Competitive Hydrogenation of Glycolaldehyde and Glucose on Ru/C with or Without AMT", AIchE Journal, Jan. 2015, vol. 61, Issue No. 1, pp. 224-238.
Mahfud et al., "Hydrogenation of Fast Pyrolyis Oil and Model Compounds in a Two-Phase Aqueous Organic System Using Homogeneous Ruthenium Catalysts", Journal of Molecular Catalysis A: Chemical, vol. 264, Issues 1-2, Mar. 1, 2007, pp. 227-236.
Zhao et al., "Catalytic Conversion of Concentrated Glucose to Ethylene Glycol with Semicontinuous Reaction System", Industrial & Engineering Chemistry Research, vol. 52, Issue No. 28, Jul. 2013, pp. 9566-9572.

(Continued)

Primary Examiner — Sikarl A Witherspoon

(57) ABSTRACT

The invention provides a continuous process for the preparation of ethylene glycol and 1, 2-propylene glycol from starting material comprising one or more saccharides, said process being carried out in a reactor system comprising a reactor vessel equipped with an external recycle loop and said process comprising the steps of: i) providing the starting material in a solvent, via an inlet, to the external recycle loop and contacting it therein with a retro-aldol catalyst composition to provide an intermediate stream; ii) then contacting said intermediate stream with hydrogen in the presence of a hydrogenation catalyst composition in the reactor vessel; iii) withdrawing a product stream comprising glycols from the reactor vessel; iv) providing a portion of said product stream, via an outlet, for separation and purification of the glycols contained therein; and v) recycling the remainder of said product stream via the external recycle loop.

9 Claims, 3 Drawing Sheets

(56) References Cited

OTHER PUBLICATIONS

Jiang et al., "Preparing Lower Polyhydric Alcohol Comprises e.g. Introducing Polyatomic Alcohol Product Solution in a Reactor and Adding Carbohydrate to the Solution, and Continuously Flowing Out the Raw Material Slurry From a Bottom of the Reactor", Thomson Scientific, Oct. 17, 2012, vol. 2013, Issue No. 38, XP002756948.

PROCESS FOR THE PREPARATION OF GLYCOLS

CROSS REFERENCE TO RELATED APPLICATIONS

This is a national stage application of International application No. PCT/EP2016/080116, filed 7 Dec. 2016, which claims benefit of priority of European application No. 15198769.0, filed 9 Dec. 2015.

FIELD OF THE INVENTION

The present invention relates to a process for the preparation of ethylene and propylene glycols from saccharide-containing feedstocks.

BACKGROUND OF THE INVENTION

Monoethylene glycol (MEG) and monopropylene glycol (MPG) are valuable materials with a multitude of commercial applications, e.g. as heat transfer media, antifreeze, and precursors to polymers, such as PET. Ethylene and propylene glycols are typically made on an industrial scale by hydrolysis of the corresponding alkylene oxides, which are the oxidation products of ethylene and propylene, produced from fossil fuels.

In recent years, increased efforts have focussed on producing chemicals, including glycols, from renewable feedstocks, such as sugar-based materials. The conversion of sugars to glycols can be seen as an efficient use of the starting materials with the oxygen atoms remaining intact in the desired product.

Current methods for the conversion of saccharides to sugars revolve around a hydrogenation/retro-aldol process as described in Angew. Chem. Int. Ed. 2008, 47, 8510-8513.

An important aim in this area is the provision of a process that is high yielding in desirable products, such as ethylene glycol and propylene glycol, and that can be carried out in a commercially viable manner. A preferred methodology for a commercial scale process would be to use continuous flow technology, wherein feed is continuously provided to a reactor and product is continuously removed therefrom. By maintaining the flow of feed and the removal of product at the same levels, the reactor content remains at a more or less constant volume.

Continuous flow processes for the production of glycols from saccharide feedstock have been described in US20110313212, CN102675045, CN102643165, WO2013015955 and CN103731258. A process for the co-production of bio-fuels and glycols is described in WO2012174087.

Typical processes for the conversion of saccharides to glycols require two catalytic species in order to catalyse retro-aldol and hydrogenation reactions.

Typically, the hydrogenation catalyst compositions tend to be heterogeneous. However, the retro-aldol catalysts are generally homogeneous in the reaction mixture. Such catalysts are inherently limited due to solubility constraints. Further, the saccharide-containing feedstock is generally in the form of a slurry in a solvent or as a homogeneous saccharide solution. The handling of such a reaction mixture requires careful consideration. Slurry reactors and ebullated bed reactors are taught as preferred options for a one-pot saccharides to glycols process in US20110313212 and WO2013015955, in order to deal with such considerations.

It is known that thermal degradation of reaction intermediates can occur in the conversion of saccharides to glycols. Such degradation reduces the overall yield of desired products and increases the complexity of the isolation process of said desired products. It has generally been found that carrying out the reaction with high concentrations of starting materials in a reactor exacerbates this degradation and the formation of by-products.

Typically, the conversion of saccharides to glycols has, therefore, been carried out as a continuous flow process with a high degree of back mixing using a saccharide-containing feedstock comprising a low concentration of saccharide in solvent. The process is carried out in the presence of usually more than one catalytic species capable of catalysing retro-aldol and hydrogenation reactions. Such a process may be carried out, for example, in a continuous flow stirred tank type reactor. In such a system, the concentration of reactants at any one point will be low, preventing any decomposition due to high concentrations. However, in such a process, as some of the back-mixed reaction mixture is continuously removed from the reactor, there will be some material that does not react to completion. This results in a product stream that contains starting material and/or intermediates, reducing the overall yield of the process and requiring separation of the starting material/intermediate from the desired product and disposal or recycling thereof.

One solution to overcome this issue was disclosed in WO2015028398, which describes a continuous process for the conversion of saccharides to glycols, in which the retro-aldol and hydrogenation reactions take place first in a stirred reactor, from which a product stream is continuously removed. The product stream is then provided to a finishing reactor, which operates essentially in a plug flow manner. As a high degree of conversion is achieved in the first reactor, the product stream entering the plug flow reactor will inevitably have a low concentration of starting materials present therein and thermal degradation is, thus reduced.

Another method is described in CN102731258, which describes a reactor in which there is suspended a catalyst filter basket in a position higher than the level of liquid reagents. The reagents are injected into the catalyst basket where they are contacted with hydrogenation catalyst compositions and then travel through the stirred slurry reactor in the bottom of the reactor vessel before flowing out of the bottom of the reactor. Said reactor vessel is equipped with a recycle loop from which reagents are re-injected into the catalyst basket.

US 2015/0329449 describes a process in which carbohydrates which can yield aldoses are reacted in a reactor having a first zone comprising mostly a retro-aldol catalyst and a second zone that contains a reducing catalyst. In said process, the aldoses are at least partially converted into glycolaldehyde in the first zone. The glycolaldehyde is then converted to ethylene glycol in the second zone of the reactor.

Further optimisation of a process for the conversion of saccharides into glycols is always desirable. It would be preferable to carry out a continuous process to provide glycols from saccharide-containing feedstock in as high a yield as possible. In such a process, it is desirable that substantially full conversion of the starting material and/or intermediates is achieved and formation of by-products is reduced. Minimising the complexity of any reactor system would also be beneficial.

SUMMARY OF THE INVENTION

Accordingly, the present invention provides a continuous process for the preparation of ethylene glycol and 1,2- propylene glycol from starting material comprising one or more saccharides, said process being carried out in a reactor system comprising a reactor vessel equipped with an external recycle loop, and said process comprising the steps of:

i) providing the starting material in a solvent, via an inlet, to the external recycle loop and contacting it therein with a retro-aldol catalyst composition to provide an intermediate stream;
ii) then contacting said intermediate stream with hydrogen in the presence of a hydrogenation catalyst composition in the reactor vessel;
iii) withdrawing a product stream comprising glycols from reactor vessel;
iv) providing a portion of said product stream, via an outlet, for separation and purification of the glycols contained therein; and
v) recycling the remainder of said product stream via the external recycle loop.

The present invention also provides a reactor system for the conversion of saccharide-containing feed stream to glycols, said system comprising a reactor vessel equipped with an external recycle loop, said external recycle loop containing an outlet for removing a product stream and an inlet, downstream of said outlet, for addition of reaction starting materials.

DETAILED DESCRIPTION OF THE INVENTION

Figure 1:
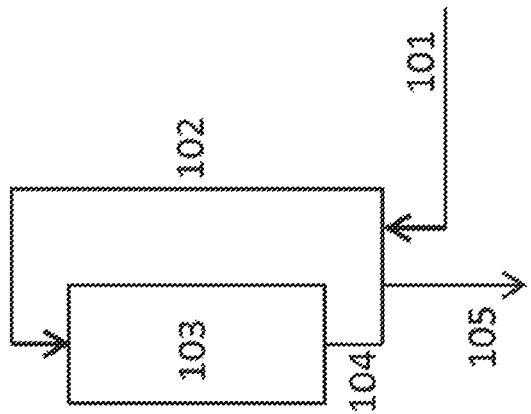
FIGS. 1 and 2 are schematic diagrams of exemplary, but non-limiting, embodiments of the process as described herein.

The present inventors have surprisingly found that high yields of desirable glycols may be obtained from saccharide starting materials by carrying out the reaction in a continuous process wherein the starting materials are provided in a solvent to an external recycle loop of a reactor vessel. Retro-aldol reactions of the saccharide starting materials are carried out in the external recycle loop and the resultant intermediate stream is then subjected to hydrogenation in the reactor vessel itself. A portion of the product stream from the reactor vessel is removed, via an outlet, for purification of the glycols contained therein and the remainder of the product stream is recycled via the external recycle loop.

The process of the present invention allows greater flexibility in the relative amounts of each catalyst composition used compared with a prior art 'one-pot' system. In particular, the present invention allows the use of high level of the hydrogenation catalyst composition without the formation of undesired hydrogenation products such as sorbitol. Such high levels of hydrogenation catalyst composition then allow rapid reaction of intermediates before thermal degradation can occur.

The starting material for the subject process comprises at least one saccharide selected from the group consisting of monosaccharides, disaccharides, oligosaccharides and polysaccharides. Examples of polysaccharides include cellulose, hemicelluloses, starch, glycogen, chitin and mixtures thereof.

If the starting material comprises oligosaccharides or polysaccharides, it is preferable that it is subjected to pre-treatment before being fed to the reactor in a form that can be converted in the process of the present invention. Suitable pre-treatment methods are known in the art and one or more may be selected from the group including, but not limited to, sizing, drying, grinding, hot water treatment, steam treatment, hydrolysis, pyrolysis, thermal treatment, chemical treatment, biological treatment. However, after said pre-treatment, the starting material still comprises mainly monomeric and/or oligomeric saccharides. Said saccharides are, preferably, soluble in the reaction solvent.

Preferably, the starting material supplied to the reactor system after any pre-treatment comprises saccharides selected from starch and/or hydrolysed starch. Hydrolysed starch comprises glucose, sucrose, maltose and oligomeric forms of glucose. Said saccharide is suitably present as a solution, a suspension or a slurry in the solvent.

The process of the present invention is carried out in the presence of a solvent. The solvent may be water or a $C_1$ to $C_6$ alcohol or polyalcohol (including sugar alcohols) or mixtures thereof. Preferred $C_1$ to $C_6$ alcohols include methanol, ethanol, 1-propanol and iso-propanol. Polyalcohols of use include glycols, particularly products of the hydrogenation/retro-aldol reaction, glycerol, erythritol, threitol, sorbitol and mixtures thereof. Preferably, the solvent comprises water.

In the process of the invention, the feed comprising the starting material in a solvent is reacted in the presence of a retro-aldol catalyst composition. Said retro-aldol catalyst composition preferably comprises one or more compound, complex or elemental material comprising tungsten, molybdenum, vanadium, niobium, chromium, titanium or zirconium. More preferably the retro-aldol catalyst composition comprises one or more material selected from the list consisting of tungstic acid, molybdic acid, ammonium tungstate, ammonium metatungstate, ammonium paratungstate, tungstate compounds comprising at least one Group I or II element, metatungstate compounds comprising at least one Group I or II element, paratungstate compounds comprising at least one Group I or II element, heteropoly compounds of tungsten, heteropoly compounds of molybdenum, tungsten oxides, molybdenum oxides, vanadium oxides, metavanadates, chromium oxides, chromium sulfate, titanium ethoxide, zirconium acetate, zirconium carbonate, zirconium hydroxide, niobium oxides, niobium ethoxide, and combinations thereof. The metal component is in a form other than a carbide, nitride, or phosphide. Preferably, the retro-aldol catalyst composition comprises one or more compound, complex or elemental material selected from those containing tungsten or molybdenum.

The retro-aldol catalyst composition may be present as a heterogeneous or a homogeneous catalyst composition. In one embodiment, the retro-aldol catalyst composition is a supported heterogeneous catalyst composition. In a preferred embodiment, the retro-aldol catalyst composition is homogeneous with respect to the reaction mixture. In this embodiment, the retro-aldol catalyst composition and any components contained therein, may be fed, via an inlet into the external recycle loop as required in a continuous or discontinuous manner during the process of the present invention.

Also, in this embodiment, the retro-aldol catalyst composition may remain in the intermediate feed and also be present in the reactor vessel and the product stream. The homogeneous retro-aldol catalyst composition may then be separated from at least a portion of the product stream provided for separation and purification of the glycols contained therein. Homogeneous retro-aldol catalyst composition separated from this stream may then be recycled to the external recycle loop.

The weight ratio of the retro-aldol catalyst composition (based on the amount of metal in said composition) to sugar feed is suitably in the range of from 1:1 to 1:1000.

The residence time of the feed stream in the external recycle loop is suitably at least 0.1 second and preferably less than 10 minutes, more preferably less than 5 minutes.

Optionally, the feed stream comprising said starting material in a solvent is contacted with the retro-aldol catalytic composition in the presence of hydrogen.

The intermediate stream will comprise reactive intermediates in the reaction of saccharides to glycols. These intermediates, in the absence of hydrogenation, mainly comprise saturated and unsaturated ketones and aldehydes. Such intermediates include, but are not limited to glycolaldehyde, pyruvaldehyde, dihydroxyacetone, glyceraldehyde, hydroxyacetone, erythrose, threose, 1-hydroxy-3,4-butanedione, 1-hydroxy-2-butanone-3-ene, 1-hydroxy-2-butanone, 1,2,3-trihydroxy-5,6-hexanedione and 1-hydroxy-2-hexanone. Highly unsaturated intermediates might polymerise, reducing the yield desired products. The intermediate stream will also comprise solvent. Some saccharide starting material may be present in the intermediate stream. However, it is preferred that no more than 5 wt %, preferably no more than 2 wt %, more preferably no more than 1 wt % of the saccharide starting material present in the feed stream is present in the intermediate stream.

The intermediate stream is then contacted with hydrogen in the presence of a hydrogenation catalyst composition in the reactor vessel. Said hydrogenation catalyst composition is preferably heterogeneous and is retained or supported within the reactor vessel. Further, said hydrogenation catalytic composition also preferably comprises one or more materials selected from transition metals from groups 8, 9 or 10 or compounds thereof, with catalytic hydrogenation capabilities.

More preferably, the hydrogenation catalytic composition comprises one or more metals selected from the list consisting of iron, cobalt, nickel, ruthenium, rhodium, palladium, iridium and platinum. This metal or metals may be present in elemental form or as compounds. It is also suitable that this component is present in chemical combination with one or more other ingredients in the hydrogenation catalytic composition. It is required that the hydrogenation catalytic composition has catalytic hydrogenation capabilities and it is capable of catalysing the hydrogenation of material present in the reactor.

In one embodiment, the hydrogenation catalytic composition comprises metals supported on a solid support. In this embodiment, the solid supports may be in the form of a powder or in the form of regular or irregular shapes such as spheres, extrudates, pills, pellets, tablets, monolithic structures. Alternatively, the solid supports may be present as surface coatings, for examples on the surfaces of tubes or heat exchangers. Suitable solid support materials are those known to the skilled person and include, but are not limited to aluminas, silicas, zirconium oxide, magnesium oxide, zinc oxide, titanium oxide, carbon, activated carbon, zeolites, clays, silica alumina and mixtures thereof.

Alternatively, the heterogeneous hydrogenation catalytic composition may be present as Raney material, such as Raney nickel, preferably present in a pelletised form.

The heterogeneous hydrogenation catalytic composition is suitably preloaded into the reactor vessel before the reaction is started. The weight ratio of the hydrogenation catalyst composition (based on the amount of metal in said composition) to sugar feed is suitably in the range of from 10:1 to 1:100.

The residence time of the intermediate stream in the reactor vessel is preferably at least 1 second and also preferably no more than 2 hours.

A product stream comprising glycols is withdrawn from the reactor vessel. Said glycols preferably comprise at least MEG, MPG and 1,2-BDO. The product stream may suitably also contain solvent, by-products and catalyst composition.

Preferably, at least 90%, more preferably at least 95%, even more preferably at least 98%, most preferably at least 99% of any carbonyl containing compounds in the intermediate stream are hydrogenated in the hydrogenation step.

The hydrogenation step and, optionally, the retro-aldol step of the process of the present invention take place in the presence of hydrogen. Preferably, both steps of the process of the present reaction takes place in the absence of air or oxygen. In order to achieve this, it is preferable that the atmosphere in the reaction zones be evacuated and replaced with first an inert gas, e.g. nitrogen or argon, and then hydrogen repeatedly, after loading of any initial reaction zone contents, before the reaction starts.

A portion of the product stream is provided for separation and purification of the glycols contained therein. Steps for purification and separation may include solvent removal, catalyst separation, distillation and/or extraction in order to provide the desired glycol products.

The inlet in the external recycle loop through which the feed stream is provided is downstream of the outlet through which a portion of the product stream is withdrawn. Other inlets may also be present in the external recycle loop. A homogeneous retro-aldol catalyst composition containing stream may be supplied separately to the feed stream comprising starting materials. A further solvent stream may also be present.

The reactor vessel used in the reactor system and process of the present invention may operate with a high degree of back-mixing or may operate in an essentially plug flow manner.

In a reactor vessel operating with a high degree of back mixing, mixing should be carried out to such an extent that the concentrations of the materials in the reactor are relatively consistent throughout. The degree of mixing for a reactor is measured in terms of a Péclet number. An ideally-stirred tank reactor vessel would have a Péclet number of 0. In this embodiment, wherein the reactor vessel operates with a high degree of mixing, the Péclet number is preferably at most 0.4, more preferably at most 0.2, even more preferably at most 0.1, most preferably at most 0.05.

It will be clear to the skilled person, however, that concentrations of any materials may be considerably higher or lower in the immediate vicinity of an inlet to the reactor vessel. Suitable reactor vessels include those considered to be continuous stirred tank reactors. Examples include slurry reactors ebullated bed reactors, jet flow reactors, mechanically agitated reactors and (slurry) bubble columns. The use of these reactor vessels allows dilution of the reaction mixture to an extent that provides high degrees of selectivity to the desired glycol product (mainly ethylene and propylene glycols).

In a reactor vessel operating with essentially a plug flow, all of the feed stream moves with the same radially uniform velocity and, therefore, has the same residence time. The concentration of the reactants in the plug flow reactor vessel will change as it progresses through the reactor vessel. Although the reaction mixture preferably essentially completely mixes in radial direction and preferably does essentially not mix in the axial direction (forwards or backwards), in practice some mixing in the axial direction (also referred to as back-mixing) may occur. Suitable reactor vessels operating with essentially plug flow include, but are not limited to, tubular reactors, pipe reactors, falling film reactors, staged reactors, packed bed reactors and shell and tube type heat exchangers.

A plug flow reactor vessel may, for example, be operated in the transition area between laminar and turbulent flow or in the turbulent area, such that a homogenous and uniform reaction profile is created.

A plug flow may for example be created in a tubular reactor vessel. It may also be created in a compartmentalized tubular reactor vessel or in another reactor vessel or series of reactor vessels having multiple compartments being transported forward, where preferably each of these compartments are essentially completely mixed. An example of a compartmentalized tubular reactor vesseloperated at plug flow may be a tubular reactor vessel comprising a screw.

Preferably a Péclet number of at least 3, more preferably at least 6, and still more preferably at least 20, most preferably at least 100, is maintained within the plug flow reactor vessel.

The temperature in the external recycle loop is suitably at least 130° C., preferably at least 150° C., more preferably at least 170° C., most preferably at least 190° C. The temperature in the reactor system is suitably at most 300° C., preferably at most 280° C., more preferably at most 270° C., even more preferably at most 250° C.

The temperature in the reactor vessel is suitably at least 20° C., preferably at least 50° C., more preferably at least 80° C., most preferably at least 120° C. The temperature in the second reaction zone is suitably at most 300° C., preferably at most 280° C., more preferably at most 270° C., even more preferably at most 250° C., most preferably at most 250° C.

Preferably, the reactor system is heated to a temperature within these limits before addition of any saccharide starting material and is maintained at such a temperature until all reaction is complete.

The pressure in the reactor system is suitably at least 1 MPa, preferably at least 2 MPa, more preferably at least 3 MPa. The pressure in the reactor system is suitably at most 12 MPa, preferably at most 10 MPa, more preferably at most 8 MPa. The first and second reactor zones may operate at the same or different pressures within these ranges.

Preferably, the reactor system is pressurised to a pressure within these limits by addition of hydrogen before addition of any saccharide starting material and is maintained at such a pressure until all reaction is complete through on-going addition of hydrogen.

In one embodiment of the invention, the portion of the product stream which has been removed for separation and purification of the glycols contained therein may be subjected to further reaction in a finishing reactor in order to ensure that the reaction has gone to completion. This is particularly preferred in the embodiment wherein the reactor vessel operating as the second reaction zone operates with a high degree of back-mixing.

Preferably said finishing reactor operate in an essentially plug flow manner. Further hydrogenation catalyst composition may be present in said finishing reactor. In the embodiment wherein the retro-aldol catalyst composition is homogeneous with respect to the reaction mixture, said retro-aldol catalyst composition will be present in the portion of the product stream which has been removed from the reactor system.

DETAILED DESCRIPTION OF THE DRAWINGS

Figure 2:
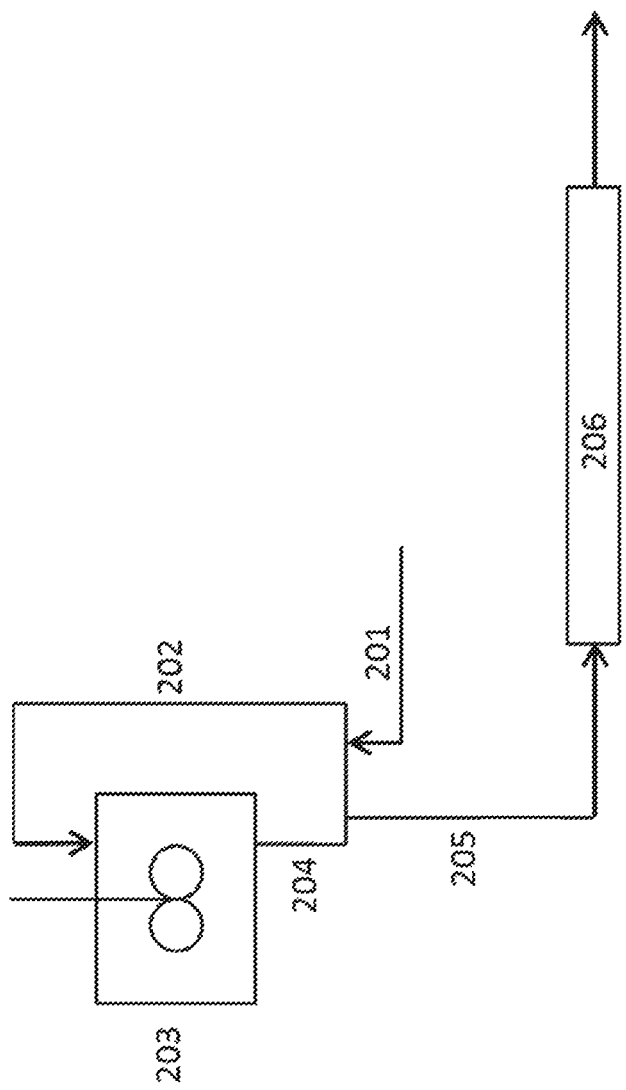

In these Figures, the first digit of each reference number refers to the Figure number (i.e. 1XX for FIG. 1 and 2XX for FIG. 2). The remaining digits refer to the individual features and the same features are provided with the same number in each Figure. Therefore, the same feature is numbered 104 in FIG. 1 and 204 in FIG. 2.

FIG. 1 illustrates a preferred, but non-limiting, embodiment of the present invention.

The feed stream 101 comprising the starting materials is provided to an external recycle loop 102 of a reactor vessel 103, via an inlet in said external recycle loop, and is contacted with the homogeneous retro-aldol catalyst composition within said external recycle loop 102.

The intermediate stream is then provided from the external recycle loop 102 into the reactor vessel 103 wherein it is contacted with hydrogen in the presence of a hydrogenation catalyst composition. The product stream 104 is then withdrawn from the reactor vessel 103 and a portion 105 of it is removed, via an outlet, for purification and separation of the glycols contained therein. The remainder of the product stream is then recycled to the reactor vessel 103 via the external recycle loop 102.

FIG. 2 illustrates a further preferred, but non-limiting, embodiment of the present invention.

In this embodiment of the invention, the reactor vessel 203 is a stirred reactor vessel operating with a high degree of back-mixing. The portion 205 of the product stream which is removed, via an outlet, for purification and separation of the glycols contained therein, is subjected to further reaction in a finishing reactor 206, before said purification and separation.

Figure 3:
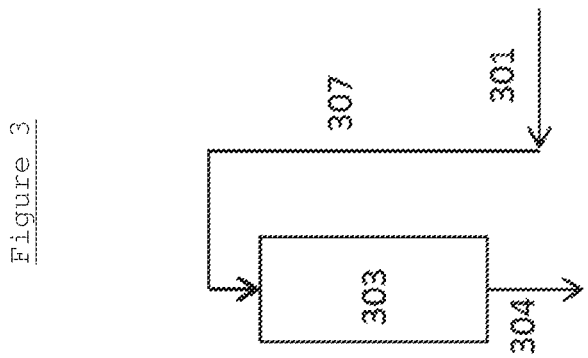
FIG. 3 represents the process modelled in Example 1.

FIG. 3 illustrates the reaction zone set-up modelled in Example 1. In this embodiment, feed stream 301 is provided to a first reaction zone 307. In the model, this reaction zone is not chosen to be an external recycle loop. After reaction in the first reaction zone 307, the intermediate stream is provided to a reactor vessel 203, which can be modelled as operating either in an essentially plug flow manner, or with a high degree of back-mixing. Product stream 304 is removed from the reactor vessel 303.

The present invention is further illustrated in the following Examples.

EXAMPLES

A kinetic model was developed in order to accurately model the combined retro-aldol reactions and hydrogenation of saccharides. These reactions result in a range of products, including ethylene glycol, propylene glycol, 1,2-butanediol, 1,2-hexanediol, glycerol, erythritol, threitol and sorbitol. Known intermediates include glycolaldehyde, hydroxyacetone and 1-hydroxy-2-butanone.

Reaction rates are not available in the literature for each individual reaction. Therefore, reaction rates were averaged on the basis of literature available (Zhang, J., Hou, B., Wang, A., Li, Z., Wang, H., Zhang, T., AIChE Journal (2014) 60 (11) 3804-3813; Zhang, J., Hou, B., Wang, A., Li, Z., Wang, H., Zhang, T., AIChE Journal (2015) 61 (1) 224-238), with the exception of hydrogenation of glycolaldehyde, which was assumed to be five times faster than the average rate of hydrogenation of all other ketone and aldehyde intermediates (referring to Mahfud, F. H., Ghijsen, F., Heeres, H. J., Journal of Molecular Catalysis A: Chemical (2007) 264 (1-2) 227-236).

The kinetic model was set up in Microsoft Excel 2010 and the respective pre-exponential factors and activation energies were slightly adjusted to enable fitting of experimental data of glucose conversion during time at various temperatures. As a final check, concentrations and conditions provided in literature (Zhao, G., Zheng, M., Zhang, J., Wang, A., Zhang, T., Ind. Eng. Chem. Res. (2013) 52 (28) 9566-9572) were used as input, resulting in model predictions in reasonable accordance with the product yields reported.

The kinetic model was then used to predict the outcome of a process of the present invention.

Example 1

In this example, the process was modelled as a 'once through' process, as shown in FIG. 3, i.e. without the recycle.

A feed stream 301 comprising 40% w glucose and 3333 ppmw tungsten in water enters reaction zone 307 where the temperature is raised to 230° C. Reaction times for retro-aldol reactions in reaction zone 307 were varied as given in Table 1 and the intermediate compositions calculated assuming ideal plug flow behaviour with the kinetic model described above (Table 1). Glucose conversion is higher than 99% and virtually complete after 0.016 min. Reactor 303 is assumed to be loaded with 60% vol hydrogenation catalyst composition and sufficient hydrogen feed is supplied for operation in trickle-bed mode. Sufficient residence time is allowed to achieve full conversion, assuming ideal plug flow behaviour. The calculated intermediate compositions were applied as feed composition for hydrogenation in reactor 303, and final product yields, leaving via 304 are given in Table 2. High glycol yields are apparent from the table, up to 66% w MEG.

Yields are given in weight percent and calculated as weight of intermediate or product divided by weight of saccharide feed and multiplied by 100.

TABLE 1

Intermediate yields

| Residence time (sec) | Glycol-aldehyde (% w) | HA* (% w) | 1OH2BO** (% w) | glycer-aldehyde (% w) | erythrose/threose (% w) | glucose (% w) |
|---|---|---|---|---|---|---|
| 0.24 | 32.954 | 1.817 | 0.208 | 1.981 | 21.700 | 30.801 |
| 0.48 | 54.254 | 4.342 | 1.074 | 3.964 | 13.367 | 9.487 |
| 0.72 | 62.404 | 6.106 | 2.161 | 4.534 | 6.176 | 2.922 |
| 0.9 | 63.733 | 7.020 | 2.926 | 4.409 | 3.192 | 1.208 |
| 0.96 | 63.674 | 7.270 | 3.162 | 4.312 | 2.536 | 0.900 |
| 1.2 | 62.131 | 8.083 | 4.000 | 3.801 | 0.977 | 0.277 |
| 1.44 | 59.660 | 8.692 | 4.684 | 3.241 | 0.361 | 0.085 |
| 3 | 45.094 | 10.625 | 6.969 | 0.992 | 0.000 | 0.000 |
| 4.8 | 35.022 | 11.237 | 7.697 | 0.248 | 0.000 | 0.000 |

*hydroxyacetone
**1-hydroxybutanone

TABLE 2 product yields

| Residence time (sec) | MEG (% w) | MPG (% w) | 1,2-butanediol (% w) | glycerol (% w) | erythritol/threitol (% w) | sorbitol (% w) |
|---|---|---|---|---|---|---|
| 0.24 | 46.544 | 3.242 | 0.694 | 3.071 | 17.841 | 19.425 |
| 0.48 | 62.009 | 5.433 | 1.698 | 4.353 | 9.734 | 5.983 |
| 0.72 | 66.858 | 6.917 | 2.763 | 4.507 | 4.304 | 1.843 |
| 0.9 | 66.929 | 7.701 | 3.479 | 4.245 | 2.184 | 0.762 |
| 0.96 | 66.595 | 7.919 | 3.697 | 4.123 | 1.728 | 0.568 |
| 1.2 | 64.376 | 8.640 | 4.470 | 3.575 | 0.656 | 0.175 |
| 1.44 | 61.595 | 9.194 | 5.101 | 3.026 | 0.240 | 0.054 |
| 3 | 46.487 | 10.989 | 7.218 | 0.921 | 0.000 | 0.000 |
| 4.8 | 36.123 | 11.560 | 7.895 | 0.230 | 0.000 | 0.000 |

Example 2

One part of a feed stream 101 (FIG. 1) comprising 40% w glucose and 3333 ppmw tungsten in water enters recycle loop 102 and is mixed with 9 parts reactor effluent, while the temperature of the mixture is raised to 230° C. Reaction times for retro-aldol reactions in recycle loop 102 were varied as given in Table 3 and the intermediate compositions calculated assuming ideal plug flow behaviour with the kinetic model described above (Table 3). Glucose conversion is higher than 99% and virtually complete after 0.016 min. Reactor 103 is assumed to be loaded with 60% vol hydrogenation catalyst composition and sufficient hydrogen feed is supplied for operation in trickle-bed mode. Sufficient residence time is allowed to achieve full conversion, assuming ideal plug flow behaviour. The calculated intermediate compositions were applied as feed composition for hydrogenation in reactor 103, and final product yields, leaving the reactor via 104, being partly recycled and partly leaving the reactor section via 105, are given in Table 4. High glycol yields are apparent from the table, up to 75% w MEG. Yields are given in weight percent and calculated as weight of intermediate or product divided by weight of saccharide feed and multiplied by 100.

TABLE 3 intermediate yields

| Residence time (sec) | Glycol-aldehyde (% w) | HA* (% w) | 1OH2BO** (% w) | glycer-aldehyde (% w) | erythrose/threose (% w) | glucose (% w) |
|---|---|---|---|---|---|---|
| 0.24 | 33.185 | 1.817 | 0.208 | 1.981 | 21.700 | 30.801 |
| 0.48 | 55.958 | 4.342 | 1.074 | 3.964 | 13.367 | 9.487 |
| 0.72 | 66.703 | 6.106 | 2.161 | 4.534 | 6.176 | 2.922 |
| 0.9 | 70.270 | 7.020 | 2.926 | 4.409 | 3.192 | 1.208 |
| 0.96 | 70.966 | 7.270 | 3.162 | 4.312 | 2.536 | 0.900 |
| 1.2 | 72.362 | 8.083 | 4.000 | 3.801 | 0.977 | 0.277 |
| 1.44 | 72.605 | 8.692 | 4.684 | 3.241 | 0.361 | 0.085 |
| 3 | 70.176 | 10.625 | 6.969 | 0.992 | 0.000 | 0.000 |
| 4.8 | 67.180 | 11.237 | 7.697 | 0.248 | 0.000 | 0.000 |

*hydroxyacetone
**1-hydroxybutanone

TABLE 4 product yields

| Residence time (sec) | MEG (% w) | MPG (% w) | 1,2-butanediol (% w) | glycerol (% w) | erythritol/threitol (% w) | sorbitol (% w) |
|---|---|---|---|---|---|---|
| 0.24 | 46.843 | 3.242 | 0.694 | 3.071 | 17.841 | 19.425 |
| 0.48 | 63.919 | 5.433 | 1.698 | 4.353 | 9.734 | 5.983 |
| 0.72 | 71.491 | 6.917 | 2.763 | 4.507 | 4.304 | 1.843 |
| 0.9 | 73.878 | 7.701 | 3.479 | 4.245 | 2.184 | 0.762 |
| 0.96 | 74.323 | 7.919 | 3.697 | 4.123 | 1.728 | 0.568 |
| 1.2 | 75.129 | 8.640 | 4.470 | 3.575 | 0.656 | 0.175 |
| 1.44 | 75.136 | 9.194 | 5.101 | 3.026 | 0.240 | 0.054 |
| 3 | 72.489 | 10.989 | 7.218 | 0.921 | 0.000 | 0.000 |
| 4.8 | 69.395 | 11.560 | 7.895 | 0.230 | 0.000 | 0.000 |

That which is claimed is:

1. A continuous process for the preparation of ethylene glycol and 1,2-propylene glycol from starting material comprising one or more saccharides, said process being carried out in a reactor system comprising a reactor vessel equipped with an external recycle loop and said process comprising the steps of:

i) providing the starting material in a solvent, via an inlet, to the external recycle loop and contacting it therein with a retro-aldol catalyst composition to provide an intermediate stream;
ii) then contacting said intermediate stream with hydrogen in the presence of a hydrogenation catalyst composition in the reactor vessel;
iii) withdrawing a product stream comprising glycols from the reactor vessel;
iv) providing a portion of said product stream, via an outlet, for separation and purification of the glycols contained therein; and
v) recycling the remainder of said product stream via the external recycle loop.

2. The process as claimed in claim 1, wherein the feed stream comprising said starting material in a solvent is contacted with the retro-aldol catalytic composition in the presence of hydrogen.

3. The process as claimed in claim 1, wherein the retro-aldol catalyst composition comprises one or more compound, complex or elemental material comprising tungsten, molybdenum, vanadium, niobium, chromium, titanium or zirconium.

4. The process as claimed in claim 1, wherein the hydrogenation catalytic composition comprises one or more metals selected from the list consisting of iron, cobalt, nickel, ruthenium, rhodium, palladium, iridium and platinum.

5. The process as claimed in claim 1, wherein the hydrogenation catalytic composition is heterogeneous.

6. The process as claimed in claim 4, wherein the one or more metals are supported on a solid support.

7. The process as claimed in claim 1, wherein the reactor vessel operates in an essentially plug flow manner.

8. The process as claimed in claim 1, wherein the reactor vessel operates with a high degree of back-mixing.

9. The process as claimed in claim 8, wherein the portion of the product stream which has been removed for separation and purification of the glycols contained therein is subjected to further reaction in a finishing reactor.

* * * * *